United States Patent [19]

Schöndorf

[11] Patent Number: 5,476,481
[45] Date of Patent: Dec. 19, 1995

[54] ELECTROTHERAPY APPARATUS WITH SUPERIMPOSED AC FIELDS

[75] Inventor: Erhard Schöndorf, Saarbrücken, Germany

[73] Assignees: Robert Ley; Ralf Scherer, both of Luxembourg

[21] Appl. No.: 240,644

[22] PCT Filed: Sep. 14, 1992

[86] PCT No.: PCT/DE92/00801

§ 371 Date: Jun. 20, 1994

§ 102(e) Date: Jun. 20, 1994

[87] PCT Pub. No.: WO93/09843

PCT Pub. Date: May 27, 1993

[30] Foreign Application Priority Data

Nov. 15, 1991 [DE] Germany .......................... 41 37 579.3

[51] Int. Cl.⁶ ..................................................... A61N 1/40
[52] U.S. Cl. ................................. 607/2; 607/68; 607/69
[58] Field of Search ................................. 607/2, 67, 68, 607/69, 71

[56] References Cited

U.S. PATENT DOCUMENTS

| | | | |
|---|---|---|---|
| 2,004,751 | 6/1935 | Fischer et al. | 607/69 |
| 2,434,497 | 1/1948 | Kearsley | 607/69 |
| 2,622,601 | 12/1952 | Nemec | 607/67 |
| 3,294,092 | 12/1966 | Landover | 607/71 |
| 4,153,061 | 5/1979 | Nemec | 607/67 |
| 4,409,565 | 10/1983 | Scherer | 607/68 |
| 4,535,777 | 8/1985 | Castel | 607/68 |
| 4,989,605 | 2/1991 | Rossen | 607/46 |
| 5,109,848 | 5/1992 | Thomas et al. | 607/68 |

FOREIGN PATENT DOCUMENTS

| | | |
|---|---|---|
| 47796 | 4/1985 | Austria . |
| 52927 | 10/1986 | Austria . |
| 0035138 | 9/1981 | European Pat. Off. . |
| 992688 | 10/1951 | France . |
| 2570529 | 3/1986 | France . |
| 8414456 | 12/1986 | France . |
| 624850 | 8/1991 | France . |
| 0974944 | 6/1961 | Germany .................. 607/68 |
| 2908365 | 9/1980 | Germany . |
| 2929293 | 2/1981 | Germany . |
| 3010716 | 9/1981 | Germany . |
| 624850 | 8/1981 | Switzerland . |
| 8904046 | 10/1984 | WIPO ...................... 607/7 |
| 9011798 | 10/1990 | WIPO . |
| 9309843 | 5/1993 | WIPO . |

OTHER PUBLICATIONS

J. Low and A. Reed: Electrotherapy Explained, Butterworth–Heinemann Ltd., 1990, pp. 28–42, ISBN 0-07 506 00497.

Otto Steuernagel, Skripten zur Elektrotherapie, 3rd ed., 1976, vol. II, p. 6, published by author.

H. Jantsch and F. Schuhfried: Niederfrequente Ströme zur Diagnostik und Therapie, 1974, p. 147.

Meinke–Gundlach: Taschenbuch der Hochfrequentztechnik, 4th Edition, vol. 3, Systems, 1986, 0 3, Fig. 3.

B. E. Philippow: Taschenbuch Elektrotechnik, vol. 1, Allgemeine Grundlagen, 3rd Edition, 1986, p. 269.

D1: A. H. Seidman, Integrated Circuits Applications Handbook, John Wiley & Sons, 1983, pp. 387–389, Ch. 12.8 "Arbitrary Waveform Generator".

*Primary Examiner*—William E. Kamm
*Attorney, Agent, or Firm*—Felfe & Lynch

[57] ABSTRACT

An electrotherapeutic field stimulator includes at least a pair of electrodes for applying the electricity to the body in the form of an electric field and a generator for providing the electricity to the electrodes in the form of at least two superimposed alternating current fields of different frequencies to provide the treatment waveform.

18 Claims, 4 Drawing Sheets

ELECTROTHERAPY APPARATUS WITH SUPERIMPOSED AC FIELDS

BACKGROUND OF THE INVENTION

The invention relates to an electrotherapy apparatus of the type which exposes muscle tissue to an electrical current.

Electrotherapy apparatus are used in many ways for the treatment of muscles and nerves. Use is made of the circumstance that tissue, as a rule, is not electrically neutral but carries electrical charges in the form of ions. To influence tissue in a non-mechanical manner, electrical or magnetic fields must act on the ions and these fields produce forces. The nature of the forces occurring is determined substantially by the shape, the amplitude and the timing of the applied fields. If a tissue is exposed to a DC electrical field, ions constantly flow down on the one side of this tissue and up again on the other side. Since chemical compounds can be broken down by the removal of ions, the tissue changes its structure under the protracted action of direct current. If, however, a rapid change in the polarity of the applied field occurs, whether on the basis of a sinusoidal alternating current, or on the basis of positive or negative voltage pulses, no lasting changes of the tissue occur at certain frequencies, because the ions do not move very far from their original position. They then oscillate to some extent around this original position and cause, among other things, a warming of the tissue.

In order to achieve specific therapeutic effects it is already known to expose muscles or nerves to electrical and/or magnetic fields of given frequency and amplitude (J. Low and A. Reed: Electrotherapy Explained, Butterworth-Heinemann Ltd., 1990, pp. 28 to 42, ISBN 0-07 506 00497). A distinction is made between voltages which have a length or duration of more than 1 millisecond and currents having a length of less than 1 millisecond. Also, currents or voltages are distinguished which change gradually or abruptly. The gradually varying electrical factors are subdivided into sinusoidal, diadynamic, "Russian," interfering and high-frequency factors.

For the treatment of muscular crippling a stimulating current apparatus is known which is applied to a patient's skin by means of an electrode (DE-A-29 08 365). This stimulating current apparatus first emits a unipolar series of pulses of a first polarity for a certain time, and then reverses the polarity and emits a unipolar series of pulses of a second polarity. The direct-current average of the two series of pulses is zero. Pauses of given lengths can be inserted between the pulse series. The series of pulses are intended for the purpose of greatly reducing the skin irritation which can be caused by the formation of acid between the skin and the electrodes.

Also known is an apparatus for electrostimulation with which the milk glands of cows and other mammals are treated in order to increase milk output and the fat content of the milk, and to accelerate the milking process (DE-C-29 29 293). This apparatus has a frequency modulator and a polarity setting means whereby pulses of a certain shape can be generated. In particular, square wave pulses of given length and polarity can be produced.

To stimulate and control smooth muscles and blood vessel tissues a programmable electrical apparatus is known by which succeeding positive and negative pulses or pulse groups can be produced (EP-C-0 137 007=AT-E-47 796). The pulses in this case rise with a time constant of about 40 milliseconds and fall again with the same time constant, the pulse width amounting to about 3 ms. The adjustable amplitudes of the pulses are between +130 V and −130 V, while the periods are preferably 625 ms.

In another known apparatus for the electrostimulation of nerves and muscles pulses are produced whose shape and frequency are adapted to the characteristics of the so-called slow muscle fibers (EP-C-0 197 889=AT-E-52 927). The frequency and the duration of the pulse series can be regulated.

In addition to direct current, pulsed current and simple alternating currents, modulated alternating currents are also used for electrotherapy. One of the modulated alternating currents is especially the so-called interference current, which is also called beat current or Nemec current (Otto Steuernagel, Skripten zur Elektrotherapie, 3rd ed., 1976, Vol. II, p. 6, published by the author). A distinction is made between endogenic and exogenic interference currents. In endogenic interference currents two medium frequencies are produced outside of the human body, and then heterodyned inside the body. On the other hand, the exogenic interference currents are produced outside of the body and fed as already heterodyned currents to electrodes which are laid on the patient.

The basic idea of beat current therapy is to use two heterodyned fields deep within the body to achieve a stimulating effect and at the same time keep the current density on the skin low. The heterodyning of two frequencies not too far apart brings it about that, depending on the phasing, these two currents amplify at a certain point in time and at another point in time they cancel one another (H. Jantsch and F. Schuhfried: Niederfrequente Ströme zur Diagnostik und Therapie, 1974, p. 147).

Furthermore, a heterodyne current therapy is known in which three alternating currents in the medium-frequency range of about 4 kHz are superimposed, which differ in frequency from one another only by a small amount, so that beats result from the superimposition (DE-A-30 10 716). The current curves resulting from the superimposition have the shape of sinusoidal envelope curves on both sides of the potential null line, while sine half-waves of large amplitude alternate with small amplitudes, comparable to a two-sideband amplitude modulation with suppressed carrier (cf. Meinke-Gundlach: Taschenbuch der Hochfrequentztechnik, 4th Edition, Vol. 3, Systems, 1986, O 3, FIG. 3, illustration in the time part). In the center the half-waves of the beat envelopes opposite one another at any time cancel their potential, i.e., there are no direct-current components. Nevertheless the two electrodes which are brought against a muscle to be treated are still at potential, so that an alternating current symmetrical with the null line is still flowing. The muscle is thus treated locally always in the same manner; any change in the preferred direction of treatment during a given time does not occur. A frequent result is muscular cramping, which is disagreeable to the patient.

SUMMARY OF THE INVENTION

According to the invention, a first alternating current field with a fundamental frequency of 0.1 to 5 Hz is imposed by the electrodes, and a second field with a frequency of 1 to 100 Hz is imposed on the first alternating field.

By the gradual change of polarity according to the fundamental frequency, the muscle is stimulated with direct current first from one side and then from the other side, although the pulsating frequency beat stimulation is sustained. If the fundamental frequency is a low-frequency sinusoidal curve, the transition from one polarity to the other is very gentle, and the patient perceives it as pleasant.

Thus the advantages of direct-current treatment is combined by the invention with the advantages of heterodyne treatment. Particularly when the amplitude of the heterodyne beat envelopes amounts to about half of the amplitude of the fundamental frequency, therapeutic successes are achieved. In this case the heterodyne beat envelopes wander to a certain extent just above the null line into the positive, and then they change into the negative etc. The disadvantages of direct-current treatment, which sometimes consist in a pronounced galvanization or faradization at the electrodes, are avoided by the gradual change in the polarity of the fundamental oscillation. Thus injuries to the skin at the points in contact with the electrodes are prevented.

With the invention, therefore, the therapeutic nerve stimulation and deep action of direct-current signals are achieved with an alternating field, which is pleasant and pain-free, that is, does not produce the known irritation and painful reactions resulting from direct-current pulses. On account of the great irritation produced by the application and removal of the electrodes it has not been possible heretofore to achieve with movable electrodes a stimulating action equivalent to that of the direct-current signals. Also, with the invention a harmonic interaction between agonist and antagonist is achieved, i.e., between active and passive muscle groups which participate in a body movement. Also, the musculature of the spinal column can for the first time be activated symmetrically, which permits a natural regulation of blocked vertebrae joints.

DETAILED DESCRIPTION OF THE PREFERRED EMBODIMENT

Figure 1:
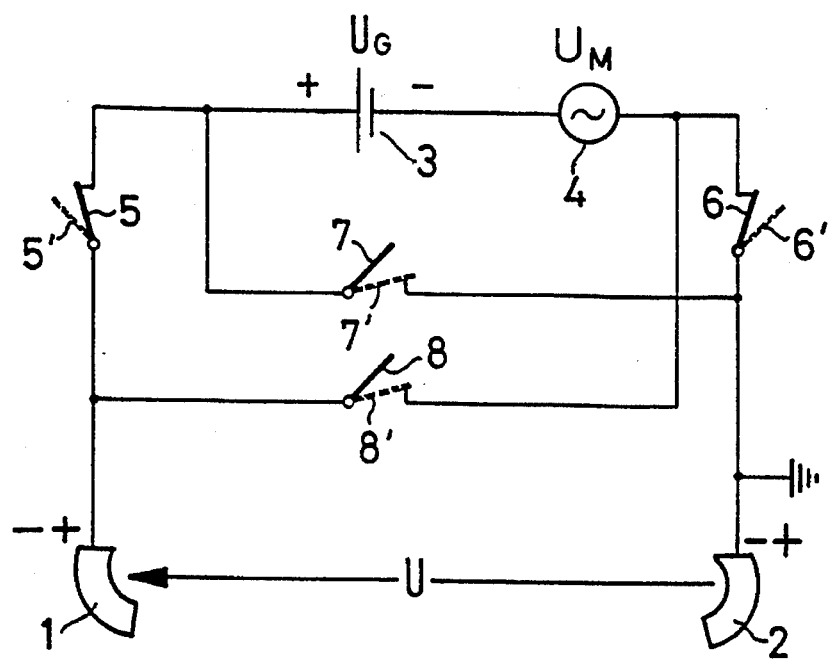
FIG. 1 shows an arrangement with two electrodes, a DC voltage source, a modulation voltage source and several switches, FIG. 2 a graphic representation of a direct current on which a beat voltage is superimposed, FIG. 3 a representation like FIG. 2, in which there is a constant switch from positive to negative polarity and vice versa, FIG. 4 a low-frequency AC curve on which a heterodyne is superimposed, FIG. 5 a block diagram of a system for the production of the current curve of FIG. 4.

In FIG. 1 two hand electrodes 1 and 2 are shown, which are brought from two sides, for example, against a muscle so that this muscle will be located between the two electrodes 1 and 2. The hand electrodes are supplied with a voltage U which is composed of a direct-current voltage $U_G$ and a modulation voltage $U_M$. The modulation voltage is preferably a heterodyne which is formed by the superimposition of two alternating voltages with a small frequency difference.

The DC voltage $U_G$ is supplied by a DC source 3 to which a modulation voltage source 4 is connected in series. The sum voltage U passes through closed switches 5 and 6 to the electrodes 1 and 2. Thus a positive potential is at the electrode 1 because this electrode 1 is connected to the positive pole of the voltage source 3. Negative potential, however, is at the electrode 2 because this electrode 2 is connected through the modulation voltage source 4 to the negative pole of the voltage source 3.

By means of the switches 5, 6 and 7, 8, the polarity at the electrodes 1, 2 can be reversed. If switches 5 to 8 assume those positions which are represented in solid lines, a positive potential is on the electrode 1 and a negative potential on electrode 2. If switches 5 to 8 assume the positions indicated in broken lines, positive potential is on electrode 2 and negative potential on electrode 1.

Figure 2:
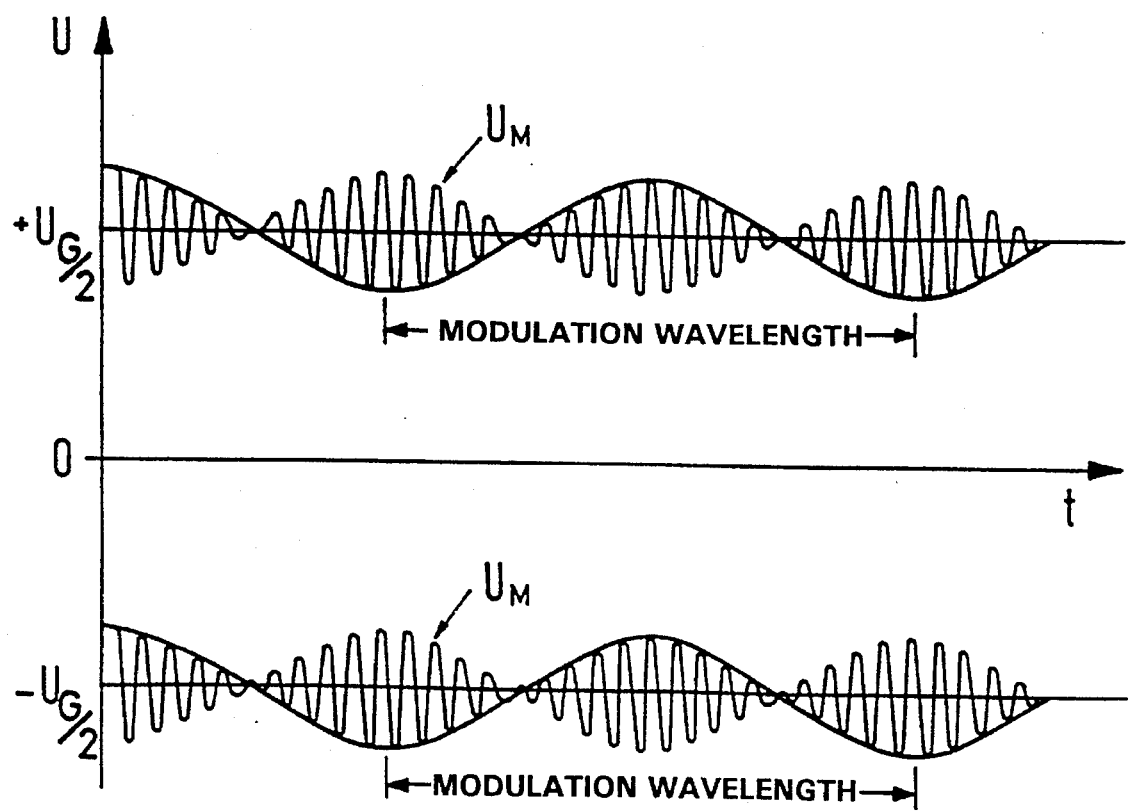

In FIG. 2, the two potentials at the electrodes 1 and 2 are represented, the upper half of FIG. 2 showing the potential at electrode 1 and the lower half the potential at electrode 2. The two potentials are symmetrical with the null line. If one of the two electrodes is set at zero potential, which can be accomplished by grounding electrode 2, there is no change in the relative potentials of the two electrodes 1 and 2. Just as before, electrode 1 is more positive than electrode 2. Instead of $U_G/2$, $U_G$ is then present at the ungrounded electrode; i.e., the potential then consists of U–OV=U, and a corresponding direct current flows with an alternating current from electrode 1 superimposed on it to electrode 2, if the positive counting direction is selected. The muscle is subjected unilaterally to the direct-current portion flowing continuously in the same direction. This unilateral application cannot be reduced by the heterodyne current symmetrically applied to the muscle. By opening switches 5 and 6 and closing additional switches 7 and 8 the polarity of the voltage can be reversed, so that the direct-current component now flows in the reverse direction. The new positions of switches 5 to 8 are represented by the switches 5' to 8' in broken lines.

The potential represented in the lower part of FIG. 2 now is present at electrode 1, while the potential represented in the upper part is on the electrode 2.

It is noted that the switches represented in FIG. 1 can be in the form of thyristors, GTO thyristors or controlled transistors.

Figure 3:
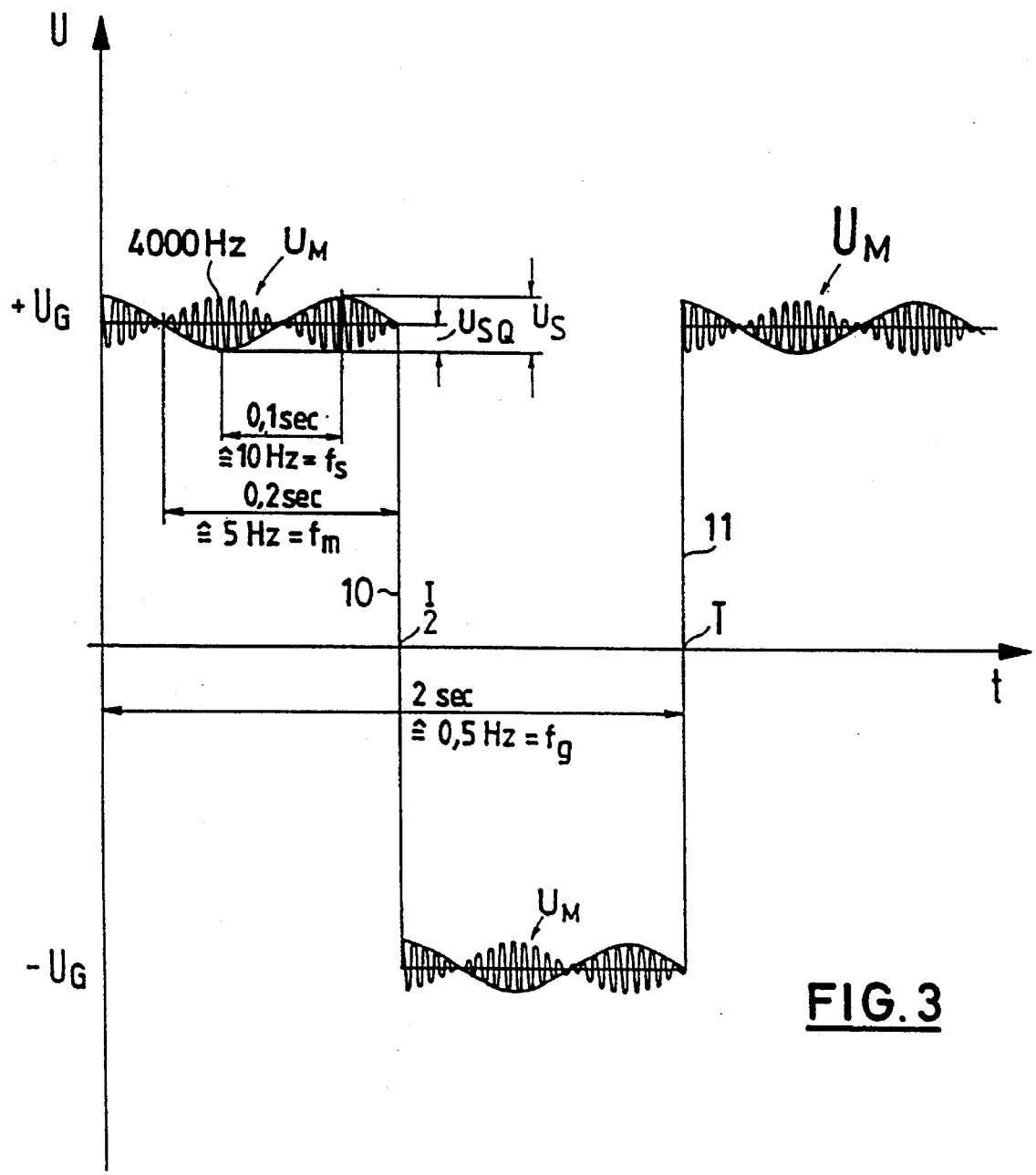

FIG. 3 shows how the voltage U varies when switches 5 to 8 are reversed at certain intervals of time. During a period T/2 the positive potential $U_G$ with the modulating potential $U_M$ is on the one electrode 1, while the other electrode 2 is at ground potential, for example, while in the next time period T/2 up to moment T the above-mentioned positive potential is on the electrode 2 and electrode 1 is at ground potential. This polarity reversal is repeated every second, for example, so that an alternating frequency of 0.5 Hz results which we shall call the fundamental frequency $f_g$. A heterodyne frequency amounting to 10 Hz, for example, and designated $f_s$ is superimposed on the alternating voltage with the fundamental frequency $f_g$. The modulation frequency pertaining to it amounts to 5 Hz and is designated $f_m$. The beat envelopes have a height of $U_s$ and correspond to twice the amount of the heterodyne amplitude $U_{SO}$. The descending and rising flanks 10 and 11 are likewise modulated with a heterodyne signal, although this is not shown in FIG. 3. On account of the abrupt voltage changes a superimposition of harmonics also occur which make a precise representation virtually impossible anyway. FIG. 2 is thus a quasi-idealized representation in which it is assumed that absolutely steep flanks 10 and 11 are possible, although this is not the case in reality. FIG. 2 also does not show the true proportions among the frequencies, but only their association with one another in principle.

The beat frequency is produced in the present case by the superimposition of an alternating voltage of 3990 Hz on an alternating voltage of 4000 Hz. For fs the following will apply:

$$f_s = f_1 - f_2 = 4000 \text{ Hz} - 3990 \text{ Hz} = 10 \text{ Hz}.$$

The amplitude of the fundamental frequency, i.e. $U_G$, in a preferred embodiment of the invention is approximately twice as high as the amplitude $U_S$ of the heterodyne envelopes. This assures that the heterodyne envelopes are raised by the sine curve into the positive range and then are lowered again into the negative range.

The fundamental frequency $f_g$ is represented in FIG. 3 as a square wave. This square wave can be transformed by a Fourier analysis into various sine and cosine waves. These waves include a sine wave with the frequency $f_g$ (see for example B. E. Philippow: Taschenbuch Elektrotechnik, Vol. 1, Allgemeine Grundlagen, 3rd edition, 1986, p. 269). Instead of a square wave a triangle wave or any other wave can be used. It is important only that this wave have a low fundamental frequency. If a sine wave with fundamental frequency is used as the basis, the result will be the voltage curve in FIG. 4.

Figure 4:
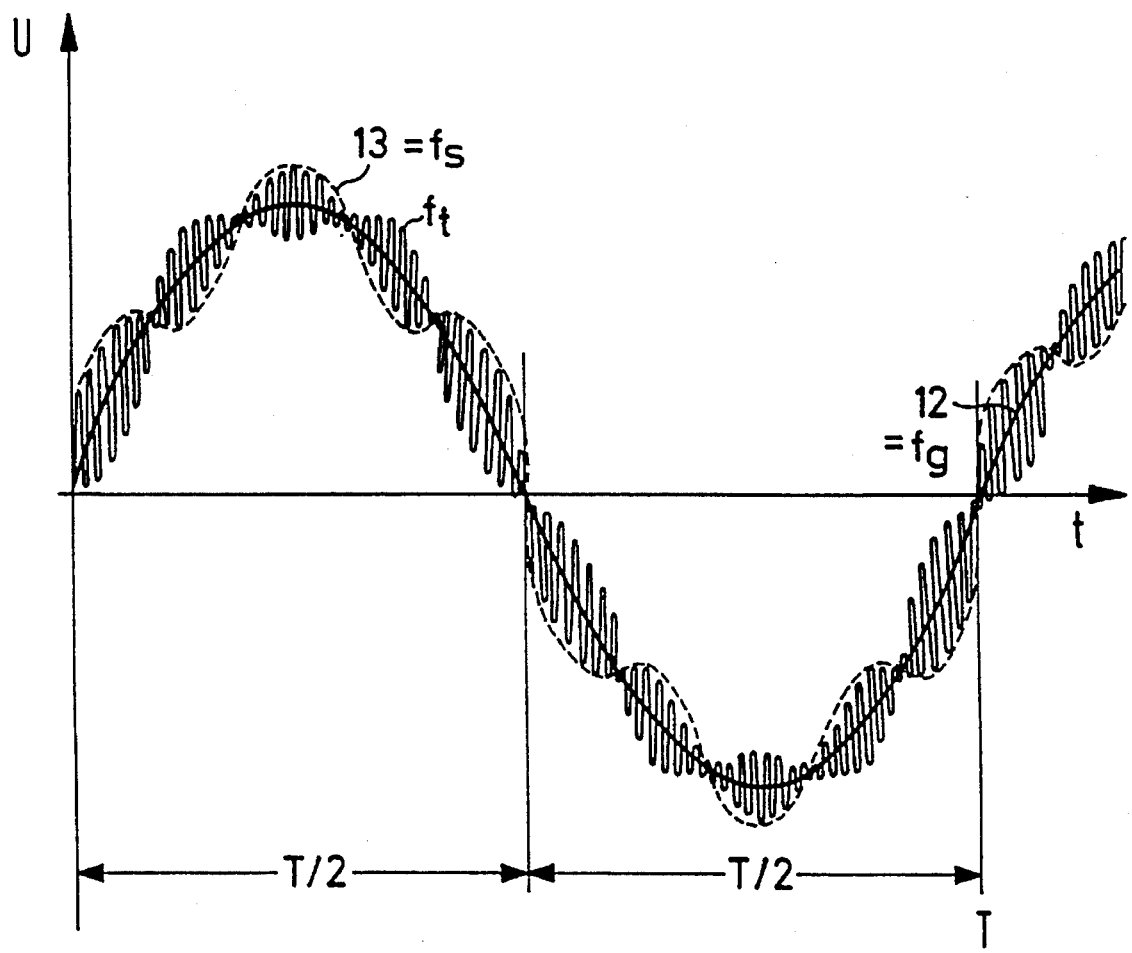

In this FIG. 4, the heterodyne envelope 13 modulates the fundamental wave 12 with the frequency $f_s = 1/T$, and the heterodyne envelope is characterized by the beat frequency $f_s$ and the carrier frequency $f_t$. The carrier frequency $f_t$ amounts, as already mentioned, to about 4000 Hz. With a voltage U according to FIG. 4 at the electrodes 1 and 2, i.e., with a heterodyned low-frequency sine wave, surprising therapeutic effects can be achieved. On the one hand the muscle being treated is subjected to a frequency of about 4000 Hz, which has the least effect on the pain receptors of the skin. A frequency between, say, 3000 Hz and 4000 Hz is therefore perceived as pleasant by the patient. On the other hand the delivery of the frequency between 3000 Hz and 4000 Hz is performed by means of the frequency envelopes of a heterodyne. This heterodyne, which consists in a continuous increase followed by a decrease of the amplitude of the carrier frequency $f_t$ has a positive influence on the tissues, as it is known from what is known as heterodyne therapy.

It is essential, however, that the voltage of the heterodyne curve be applied once to one side of the muscle and once to the other side of the muscle. This effect is achieved by the relatively slow change in the polarity of the fundamental frequency $f_g$. With the slow polarity alternation virtually the same effects are achieved as in direct-current therapy, but without having to put up with its disadvantages. Moreover, the advantages of alternating current therapy are fully retained.

Figure 5:
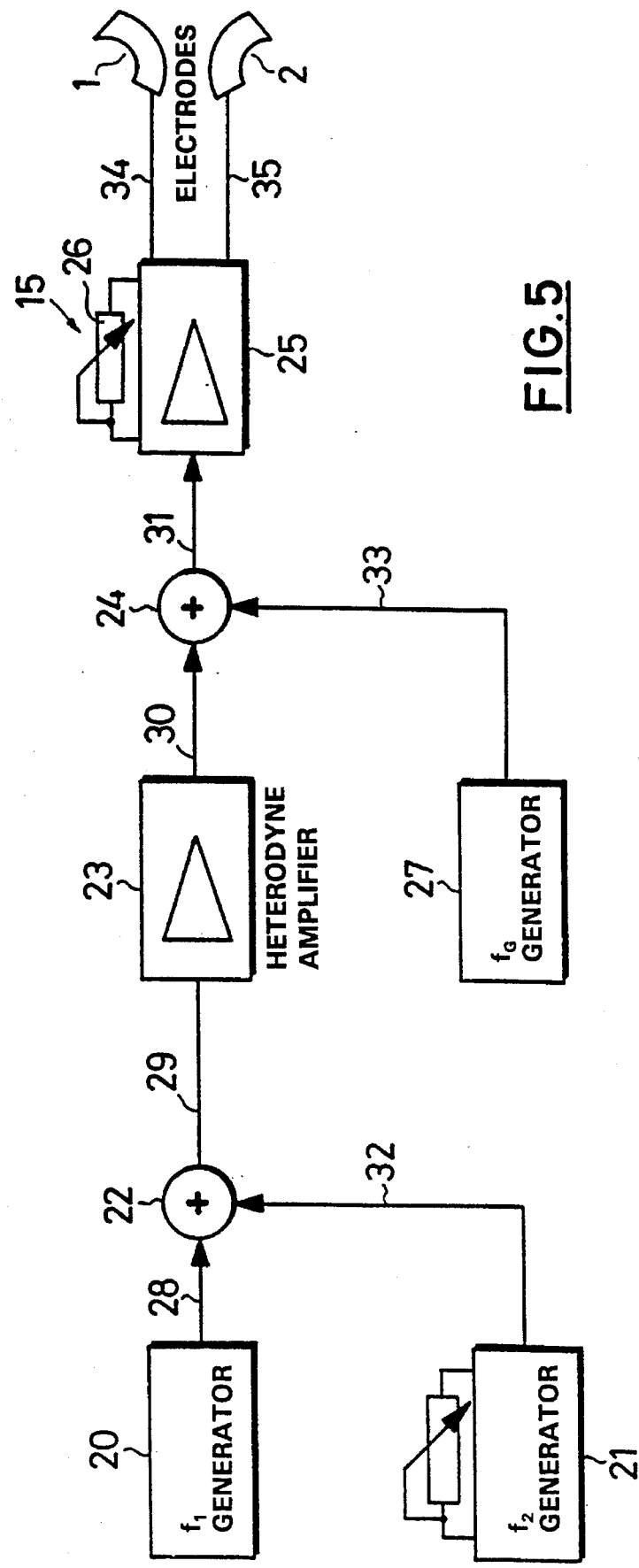

In FIG. 5 is a block diagram of a system for the production of a voltage curve according to FIG. 4.

In it can be seen two sine wave generators 20 and 21, of which the one generator 20 produces a voltage of 4000 Hz, while the other generator provides a voltage with a frequency of 3990. Through the conductors 28 and 32, respectively, the two voltages are fed to a mixer circuit 22 where the heterodyning takes place, so that a heterodyne voltage results. The term mixer circuit is to be understood to mean a system for the general, e.g., additive or multiplicative combining or superposition of curves, not a frequency converter such as what is provided, say, in a superheterodyne receiver between an RF input stage and an intermediate frequency amplifier. This heterodyne voltage is fed through a conductor 29 to a heterodyne amplifier 23 which amplifies the heterodyne voltage and feeds it to a modulator 24. The amplified heterodyne signal, which passes through a line 30 to the modulator 24, is modulated with a sinusoidal voltage of about 0.1 to 1 Hz coming from a sinusoidal signal generator 27. From here the modulated signal passes through a line 31 to an output amplifier 25 which can be regulated by a resistance 26. The two electrodes 1 and 2 are connected to the output of the output amplifier 25 by the lines 34 and 35. The amplitude of the oscillator 21 can be controlled by a resistance 36. In this manner it can be brought about that the amplitudes of the voltages of the two oscillators will always be equal, which is especially important to the beat effect. The amplifier 23 is therefore arranged between the two mixer stages 22 and 24 so as to be able to adjust the ratio between the amplitude of the fundamental and the amplitude of the heterodyne band. As already mentioned, an amplitude ratio of 2:1 is especially advantageous.

Instead of a single heterodyne a heterodyne can also be superimposed on the sinusoidal fundamental curve 12, which corresponds to a two-sideband amplitude modulation with suppressed carrier.

The arrangement represented in FIG. 5 is only one of several possible embodiments. The superimposition of the two precisely harmonic voltages of the oscillators 20 and 21 corresponds to an amplitude modulated wave with a single modulation frequency. It is therefore basically possible to use the numerous modulators known in the field of amplitude modulation for the production of the heterodynes since the amplitude-modulated waves are equivalent to the superposition of two precisely harmonic partial waves.

It is also to be noted that the analog curves represented in FIGS. 2 to 4 can be digitalized by using the scanning theorem. To produce a curve as in FIG. 4, this curve can be scanned at at least twice the frequency of the highest frequency occurring in this curve, and the resultant amplitude samples can be resolved into individual bits. These bits can be fed into a read-only memory which then to some extent stores the curve shape of FIG. 4. By means of appropriate pulse generators this curve shape can be retrieved repeatedly from the memory.

It is also to be noted that, instead of the external production of the curve shape of FIG. 4, internal production is also possible. In this case different waves are fed to the muscle from the outside, which then result in the curve shape of FIG. 4 on the muscle itself.

It is particularly to be stressed that the therapeutic effect is especially apparent if the ratio of the amplitude of the envelope of the heterodyne and the amplitude of the carrier sine wave is a minimum of 1:1 and a maximum of 1:2. It is also important that the heterodyne curve be produced by the superimposition of two voltages within the spectrum between 1 and 5,000 Hz.

I claim:

1. Electrotherapy apparatus for treating tissue, said apparatus comprising electrodes between which tissue can be disposed for treatment, means for producing a first alternating field between said electrodes, said first alternating field having a frequency between 0.1 Hz and 5 Hz; and means for superimposing a second alternating field with a frequency of 1 to 100 Hz on said first field.

2. Electrotherapy apparatus as in claim 1 further comprising means for superimposing a third alternating field on said second field so that said second field serves as an envelope of said third field, said third field having a higher frequency than said second field.

3. Electrotherapy apparatus as in claim 2 wherein said third alternating field has a frequency between 3000 and 4000 Hz.

4. Electrotherapy apparatus as in claim 2 wherein said means for superimposing a second field comprises means for superimposing voltages having two adjacent frequencies to produce a heterodyne curve which serves as said envelope.

5. Electrotherapy apparatus as in claim 4 wherein said adjacent frequencies have a difference of 10 Hz, whereby said second field has a frequency of 10 Hz.

6. Electrotherapy apparatus as in claim 5 wherein said adjacent frequencies are 4000 Hz and 3990 Hz.

7. Electrotherapy apparatus as in claim 4 wherein said means for superimposing a second field comprises a first oscillator which outputs a voltage having one of said adjacent frequencies, a second oscillator which outputs a voltage having the other of said adjacent frequencies, and a first mixer which superposes the output voltages of respective said first and second oscillators.

8. Electrotherapy apparatus as in claim 7 further comprising a second mixer which superimposes said second field on said first field.

9. Electrotherapy apparatus as in claim 8 further comprising an amplifier between said first mixer and said second mixer.

10. Electrotherapy apparatus as in claim 8 further comprising an adjustable amplifier between said second mixer and said electrodes.

11. Electrotherapy apparatus as in claim 4 wherein said superimposed voltages have the same amplitude.

12. Electrotherapy apparatus as in claim 4 wherein said first alternating field has an amplitude which is approximately twice the height of said envelope.

13. Electrotherapy apparatus as in claim 1 wherein said first alternating field is a square wave alternating field.

14. Electrotherapy apparatus as in claim 1 wherein said first alternating field is a sinusoidal alternating field.

15. Electrotherapy apparatus for treating tissue, said apparatus comprising electrodes between which tissue can be disposed for treatment, means for producing an electric field having a carrier frequency $f_t$ between said electrodes, said electric field having an amplitude, means for modulating said amplitude according to a modulation frequency $f_m$ of 1 to 100 Hz, and means for reversing the polarity of said electrodes according to a fundamental frequency $f_g$ of 0.1 to 5 Hz.

16. Electrotherapy apparatus as in claim 15 wherein said carrier frequency $f_t$ is 3000 to 4000 Hz.

17. Electrotherapy apparatus as in claim 15 wherein said fundamental frequency $f_g$ is 0.1 to 1 Hz.

18. Electrotherapy apparatus as in claim 1 wherein said means for producing said electric field is an AC power supply having a voltage $U_M$ and said means for reversing the polarity of said electrodes is an AC power supply having a voltage $U_G$, said apparatus comprising means for superimposing said voltage $U_G$ on said voltage $U_M$.

* * * * *